(12) United States Patent
Geyer et al.

(10) Patent No.: US 7,645,270 B2
(45) Date of Patent: Jan. 12, 2010

(54) DOUBLE TAKE-OFF NEEDLE AND METHOD FOR PRODUCING IT

(75) Inventors: Jerome Geyer, Wahlenheim (FR); Nolwenn Stephan, Illkirch (FR); Mathieu Arrault, Saverne (FR)

(73) Assignee: Millipore Corporation, Billerica, MA (US)

( * ) Notice: Subject to any disclaimer, the term of this patent is extended or adjusted under 35 U.S.C. 154(b) by 625 days.

(21) Appl. No.: 11/247,523

(22) Filed: Oct. 11, 2005

(65) Prior Publication Data

US 2006/0086750 A1    Apr. 27, 2006

(30) Foreign Application Priority Data

Oct. 26, 2004   (FR)  .................................. 04 11415

(51) Int. Cl.
*A61M 5/32* (2006.01)
*B67D 5/00* (2006.01)

(52) U.S. Cl. ........................ 604/411; 222/81; 604/403

(58) Field of Classification Search ................ 604/533, 604/534, 537–9, 164.01–164.12, 411; 439/595; 600/573–579; 222/81; 264/603, 605; 425/515; 266/115

See application file for complete search history.

(56) References Cited

U.S. PATENT DOCUMENTS

| 4,292,405 | A |   | 9/1981  | Mascoli et al. |
|-----------|---|---|---------|----------------|
| 4,351,900 | A |   | 9/1982  | Lemonnier et al. |
| 4,411,661 | A | * | 10/1983 | Kersten ..................... 604/411 |
| 5,030,205 | A | * | 7/1991  | Holdaway et al. ...... 604/164.02 |
| 5,372,582 | A | * | 12/1994 | Skrabal et al. ................ 604/44 |
| 5,405,329 | A | * | 4/1995  | Durand .................. 604/164.01 |
| 5,407,807 | A |   | 4/1995  | Markus et al. |
| 5,762,629 | A | * | 6/1998  | Kambin .................. 604/164.11 |
| 5,879,499 | A | * | 3/1999  | Corvi .......................... 156/175 |
| 2002/0065486 | A1 | * | 5/2002 | Balbierz et al. ......... 604/164.02 |
| 2003/0028146 | A1 | * | 2/2003 | Aves ..................... 604/164.06 |
| 2003/0069552 | A1 | * | 4/2003 | O'Keefe et al. ............. 604/278 |

(Continued)

FOREIGN PATENT DOCUMENTS

DE              4122476          1/1993

(Continued)

OTHER PUBLICATIONS

Translation of abstract of Sartorius DE19905644 from IDS dated Oct. 11, 2005.*

*Primary Examiner*—Kevin C Sirmons
*Assistant Examiner*—Michael J Anderson (57) ABSTRACT

The take-off needle comprises a main hollow lance having a distal end adapted to perform a pricking operation, said hollow lance being connected to two pipes each provided with a spigot for it to be connected to a tube, said needle further comprising a body for holding the main hollow lance, said holding body defining two internal cylindrical surfaces forming said pipes, the main hollow lance comprising, at its proximal end, a sleeve having an internal channel of which the distal end is connected to the proximal end of the main hollow lance, and of which the proximal end opens into the holding body, said sleeve comprising at its proximal end two crescent-shaped surfaces inclined towards the interior of the internal channel and towards the distal end of the sleeve, each of said crescent-shaped surfaces being disposed so as to extend in line with one of the internal cylindrical surfaces of the holding body.

12 Claims, 12 Drawing Sheets

U.S. PATENT DOCUMENTS

2003/0204169 A1* 10/2003 Howell et al. .......... 604/164.12
2003/0229330 A1* 12/2003 Hickle ....................... 604/411
2005/0033267 A1*  2/2005 Decaria ...................... 604/533
2006/0086750 A1*  4/2006 Geyer et al. ................... 222/81

FOREIGN PATENT DOCUMENTS

DE          19905644          8/2000

* cited by examiner

DOUBLE TAKE-OFF NEEDLE AND METHOD FOR PRODUCING IT

CROSS REFERENCE TO RELATED APPLICATIONS

The present application claims priority to French Patent Application No.: 0411415, filed on Oct. 26, 2004. The entire contents incorporated herewith.

SUMMARY OF INVENTION

The invention concerns the general field of take-off needles adapted to be pricked through an elastic wall in order to take off liquid contained in a container closed by the wall.

The invention more particularly concerns such a take-off needle which comprises a hollow lance generally formed from a fine steel tube provided at its distal end with a sharp pricking tip. This hollow lance is furthermore connected by its proximal end to two pipes each provided with a spigot for it to be connected to a tube.

The pricking tip is adapted to pass through said elastic wall to enable the liquid to flow in the hollow lance towards the two pipes and tubes connected to the spigots, to take off liquid in two containers.

The flow of the liquid in the lance towards the two pipes is thus divided into two such that half the liquid taken off is collected by each of the containers via a pipe.

Such needles are for example used to take off liquid from a bottle closed by a rubber bung. The two spigots are then each connected in advance to a tube leading to a container. Next the needle is pricked into the bung such that its distal end passes through the bung and reaches the medium to be taken-off.

The liquid to be taken off then flows to the two containers, each of the containers thus receiving half of the liquid taken-off, for example by gravity or with the help of a peristaltic pump or else by the pressurization of the bottle containing the liquid.

The hollow lance and the two pipes are generally arranged in a Y to efficaciously divide the flow from the hollow lance to the pipes. These needles are referred to as "double needles".

These double needles may be vented, that is to say that they comprise a second hollow lance, of smaller diameter than the main hollow lance, which is inserted in the main hollow lance. This second hollow lance allows the progressive introduction of air into the bottle containing the liquid to take off as the liquid flows in the main hollow lance. Such a vented needle makes it possible to carry out take-off operations from a fluid-tight bottle.

Such double needles are known which comprise a hollow lance of which the proximal end is held in a polymer body defining an internal channel which extends from the proximal end of the hollow lance and which divides into two to form the two pipes leading to the two spigots.

The division of the flow coming from the hollow lance is thus performed within the polymer body. The efficacy of this division may be measured by the difference in the volumes collected at the outlet of the two spigots, the volumes ideally being equal. The efficacy of the division here depends on the hydrodynamic quality of the pipes inside the polymer body, and in particular the capability of the pipes to divide the flow without creating disturbance in the flow.

The object of the invention is to improve this type of double needle.

To that end, the invention is directed to a take-off needle comprising a main hollow lance having a distal end adapted to perform a pricking operation, said hollow lance being connected to two pipes each provided with a spigot for it to be connected to a tube, said needle being characterized in that it comprises a body for holding the main hollow lance, said holding body defining two internal cylindrical surfaces forming said pipes, and in that the main hollow lance comprises, at its proximal end, a sleeve having an internal channel of which the distal end is connected to the proximal end of the main hollow lance, and of which the proximal end opens into the holding body, said sleeve comprising at its proximal end two crescent-shaped surfaces inclined towards the interior of the internal channel and towards the distal end of the sleeve, each of said crescent-shaped surfaces being disposed so as to extend in line with one of the internal cylindrical surfaces of the holding body.

The internal geometry of such a needle ensures an equal distribution of the flow to each of the two pipes.

The liquid to take off is led directly from the proximal end of the hollow lance to the two pipes, without dead space, that is to say without a zone in which the product could stagnate.

A laminar flow of liquid can thus be established between the hollow lance and the two pipes.

The extension of the cylindrical surfaces of the pipes into the sleeve of the hollow lance enables the presence of imperfections in the path of the liquid to be avoided. The flow of the liquid is consequently not disturbed in that flows along a pipe free of imperfections. Since the forms of the pipes and of the sleeve are complementary, the use of glue or any other surface preparation is furthermore avoided.

Such a needle can consequently be mass produced at low cost.

According to a preferred feature, the sleeve extends beyond the proximal end of the main hollow lance, the crescent-shaped surfaces being disposed away from the proximal end of the main hollow lance.

The sleeve may furthermore be fixed to the holding body for improved rigidity of the needle.

According to an advantageous embodiment, the sleeve is molded onto the main hollow lance. The sleeve may also comprise angular fool-proof devices which serve, for example, for positioning it in a mold.

According to an embodiment, the needle further comprises a venting hollow lance inserted in the main hollow lance, the venting hollow lance passing through the internal channel of the sleeve, so as to form a vented needle.

As for the main hollow lance, the venting hollow lance may comprise a support at its proximal end, the support being fixed to the holding body for improved rigidity of the needle. The support may also be molded onto the proximal end of the venting hollow lance.

Furthermore, the holding body may be molded onto the sleeve and onto the support, so rigidly ensuring their positioning.

According to a preferred feature, the holding body comprises a housing in which the sleeve is held; two pipes communicating with said housing; a housing for the support; said housings being aligned. The holding body may further comprise a connecting channel receiving the venting hollow lance and communicating with the two pipes.

For a good connection of the two internal pipes of the holding body with the crescent-shaped surfaces, the sleeve may be elastically deformable.

According to other advantageous features, the main hollow lance comprises a crushed heel at its distal end; the needle further comprises grasping means attached to the holding body.

The invention also relates to a method of manufacturing a take-off needle as described earlier, said method comprising the following steps:

molding the sleeve onto the main hollow lance using a V-shaped core adapted to form the crescent-shaped surfaces on the sleeve;

molding the holding body onto the sleeve using two cylindrical core pins forming a V of the same form as said core.

This method makes it possible to produce a take-off needle having the advantages cited above, in particular of avoiding the formation of imperfections in the junction zone extending between the proximal end of the main hollow lance and the two pipes, so as not to disturb the flow of the taken-off liquid.

Other features and advantages of the invention appear in the light of the following description of a preferred embodiment, given by way of non-limiting example, and made with reference to the accompanying drawings in which:

DETAILED DESCRIPTION

Figure 1:
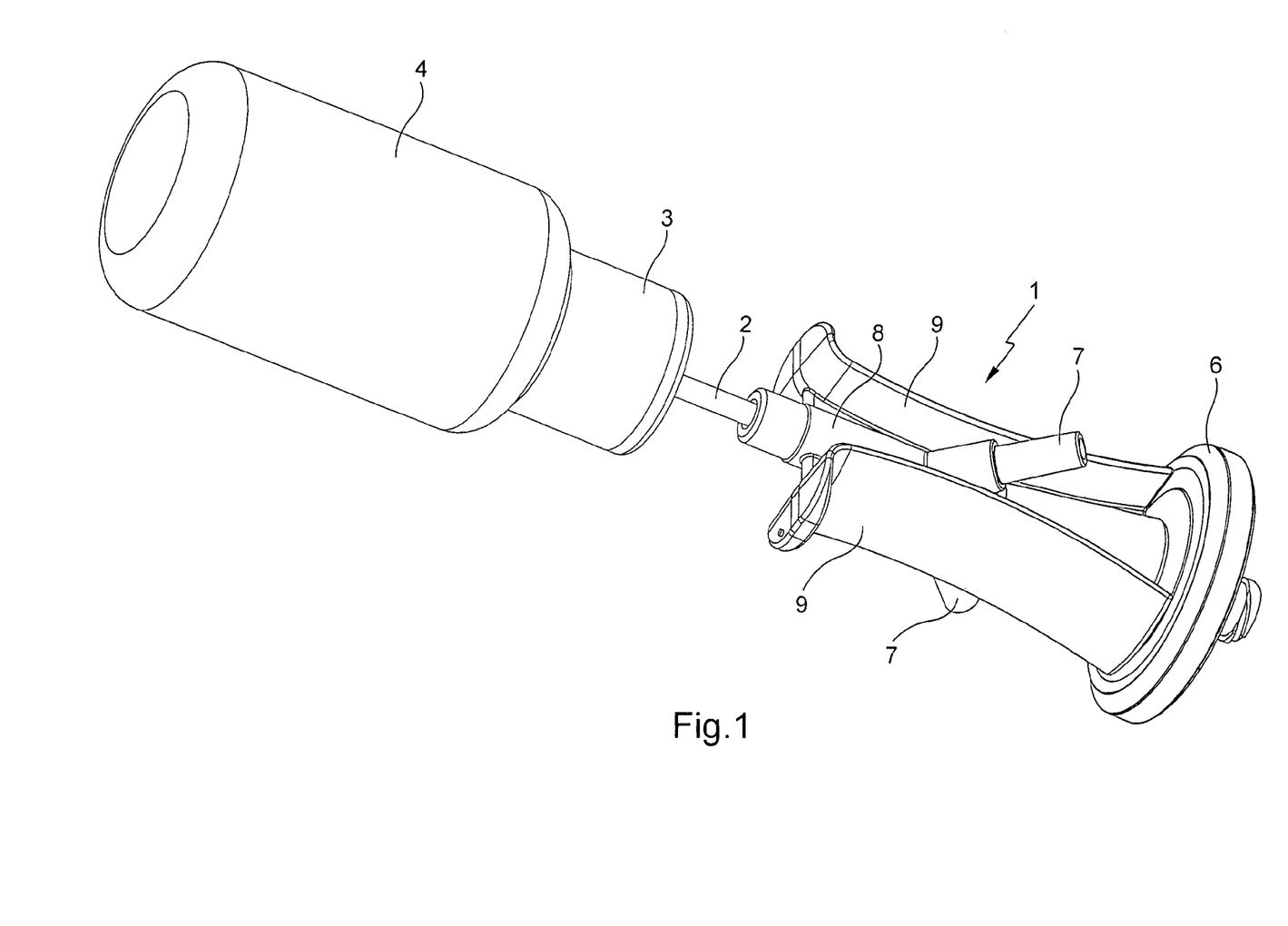
FIG. 1 is a perspective view of a needle according to the invention positioned for taking off liquid contained in a sealed bottle.

FIG. 1 shows a common situation of use of a take-off needle 1 according to the invention. The main hollow lance 2 of the needle 1 is pricked onto the rubber bung 3 of a bottle 4 connecting a liquid to be taken off.

Figure 2:
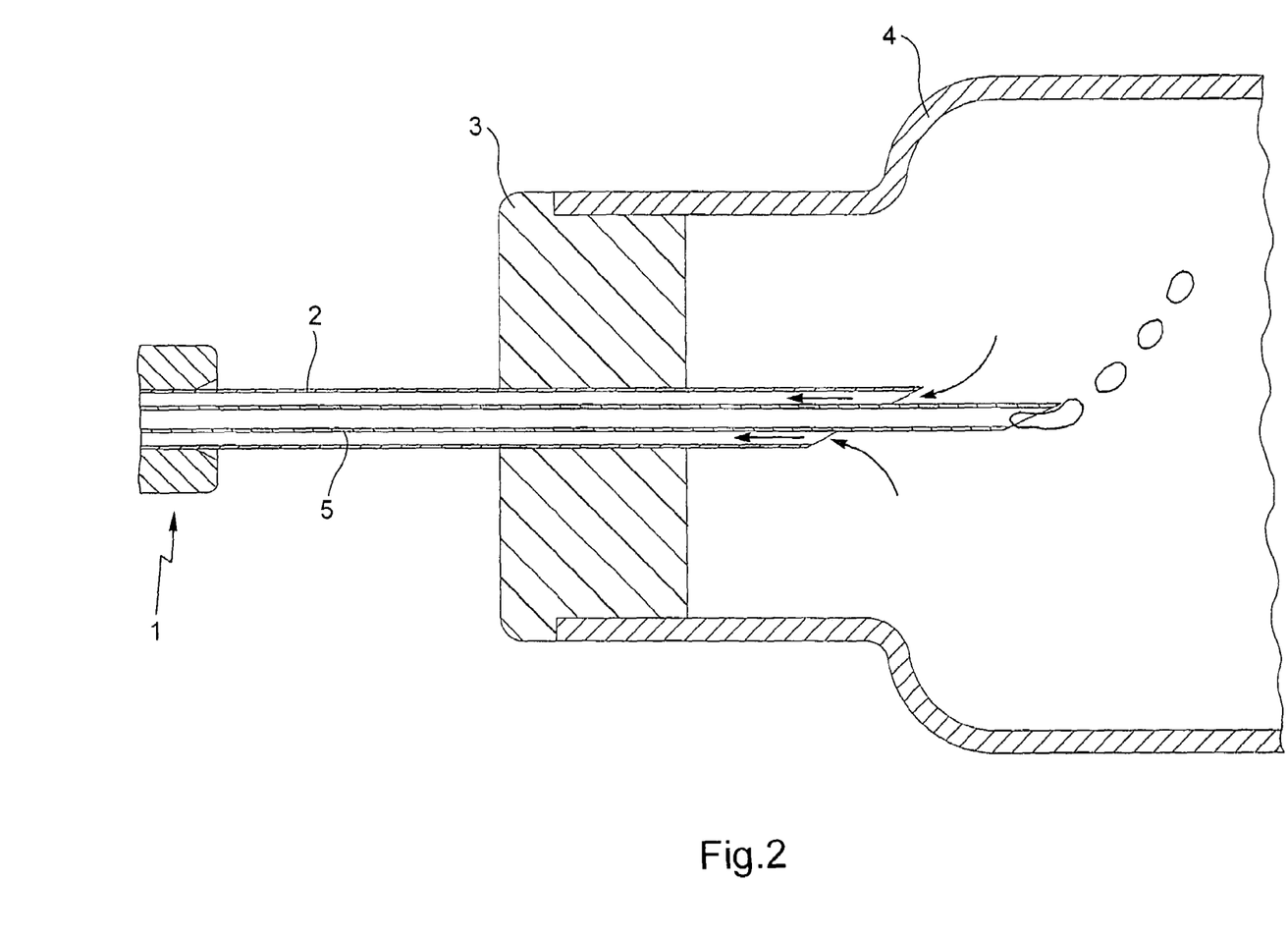
FIG. 2 is a partial view in cross-section showing the cooperation of the take-off needle and the bung of the bottle of the arrangement of FIG. 1.

FIG. 2 is a view in cross-section showing the bung 3 with the main hollow lance 2 passing through it. The needle 1 is a vented needle in that it comprises a venting hollow lance 5 disposed coaxially relative to and within the main hollow lance 2. The arrows that can be seen in FIG. 2, within the bottle 4, show the path along the main hollow lance 2 of the liquid taken off while air bubbles come out of the venting hollow lance 5 inside the bottle 4 progressively as the liquid contained in the bottle 4 is taken off.

The venting filter 6 which can be seen in FIG. 1, behind the needle 1, is connected to the venting hollow lance 5 and allows sterile air to be introduce into the bottle 4.

The needle 1 comprises two spigots 7 projecting laterally from a holding body 8. These spigots 7 are connected to two internal pipes of the holding body 8 which are connected to the main hollow lance 2. The spigots 7 must consequently each be connected to a take-off tube (not shown) which thus enables the taken-off liquid to be collected.

The flow of taken-off liquid flowing in the main hollow lance 2 is thus divided into two equal flows each directed to one of the spigots 7, which enables two equal volumes of taken off liquid to be obtained by a single take-off operation.

The needle 1 furthermore comprises two gripping cheeks 9 adapted for its manual manipulation by the user.

Figure 3:
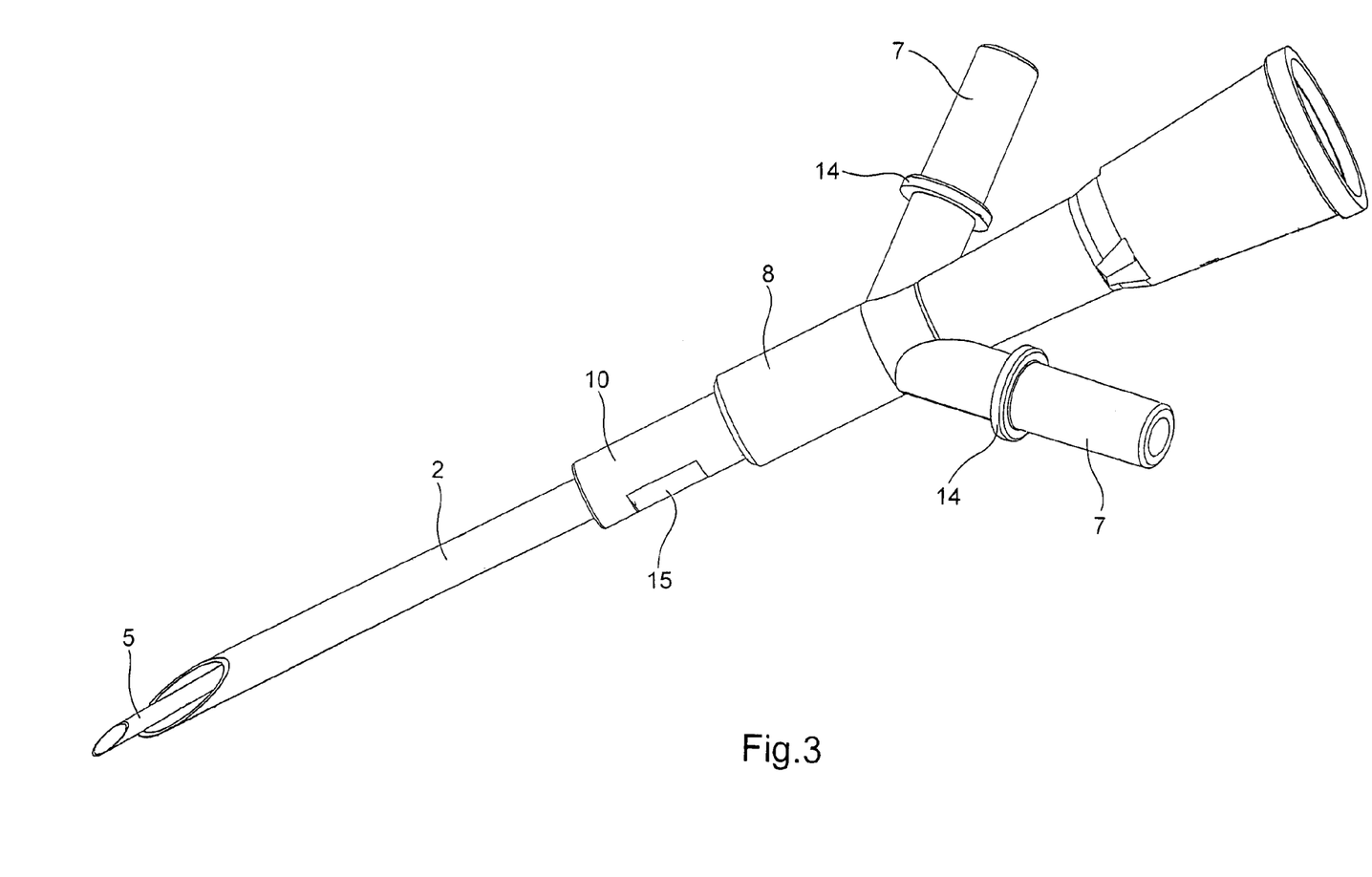
FIG. 3 is a perspective view of the take-off needle of FIG. 1 which is shown with its accessories removed.

FIG. 3 is a perspective representation of the take-off needle 1 after removal of the gripping cheeks 9 and the venting filter 6.

Figure 4:
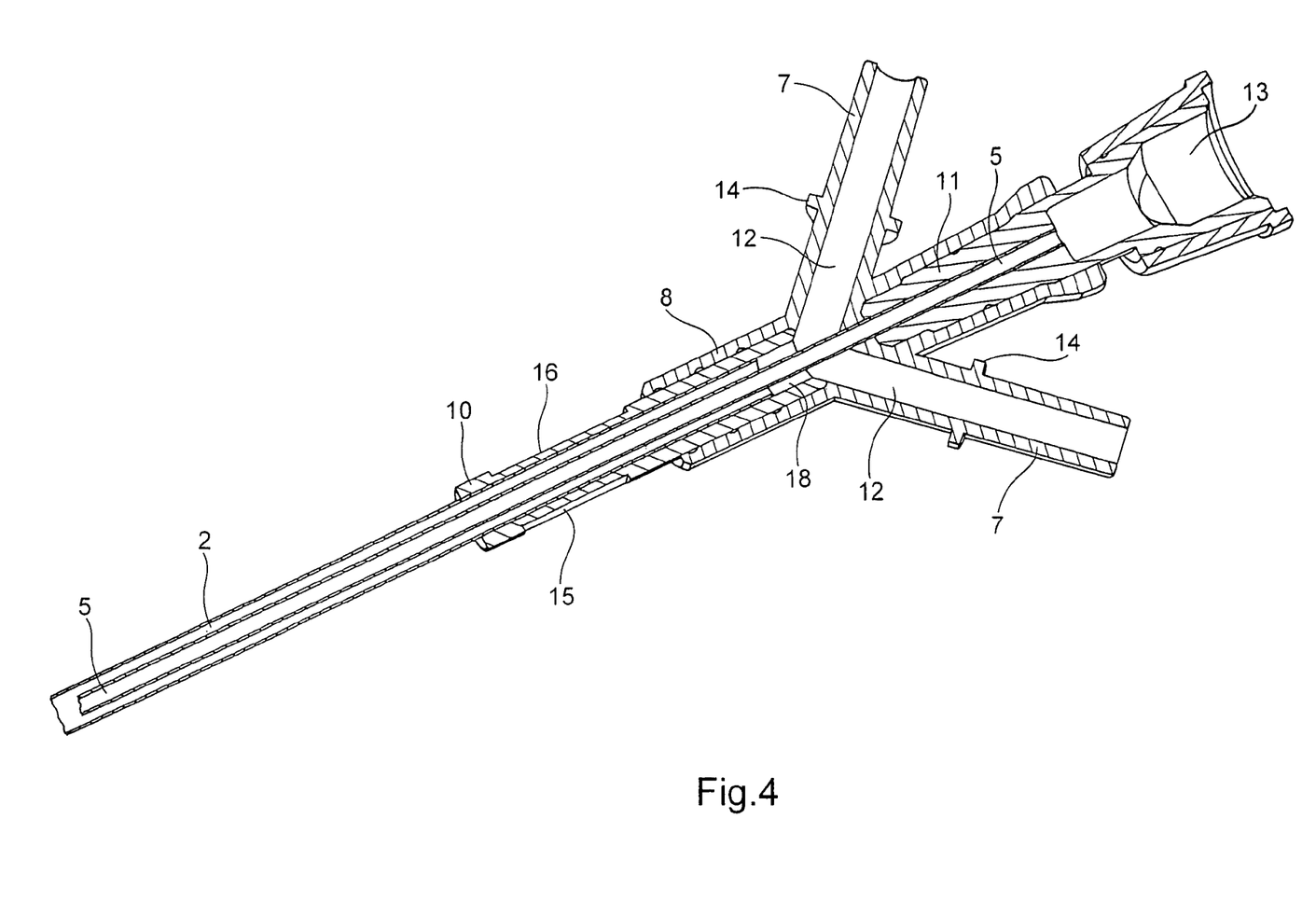
FIG. 4 is a longitudinal cross-section of the take-off needle represented in FIG. 3.

The cross-section of FIG. 4 shows the internal constitution of the needle 1.

The main hollow lance 2 is fixed in a sleeve 10 over a portion of its length. In the same way, the venting hollow lance 5 is fixed in a support 11 also over a portion of its length.

The back of the support 11 is open to the exterior to enable the venting hollow lance 5 to be in contact with the air, either directly, or via a venting filter 6 (see FIG. 1) which can be inserted in a housing 13 provided for that purpose in the support 11.

The holding body 8 forms a rigid structure holding the sleeve 10 and the support 11 in relation to each other such that the venting hollow lance 5 is inserted in the main hollow lance 2, the two hollow lances 2, 5 being coaxial.

The holding body 8 defines in addition two pipes 12 forming a Y with the main hollow lance 2 to enable the flow in the hollow lance 2 to be divided into two separate and equal flows.

The needle 1 further comprises, on each spigot 7, a collar 14 acting as an abutment for the tubes which are adapted to be connected to the spigots 7.

The method of manufacturing the take-off needle 1 of the present example will now be described with reference to FIGS. 5 to 12.

Figure 5:
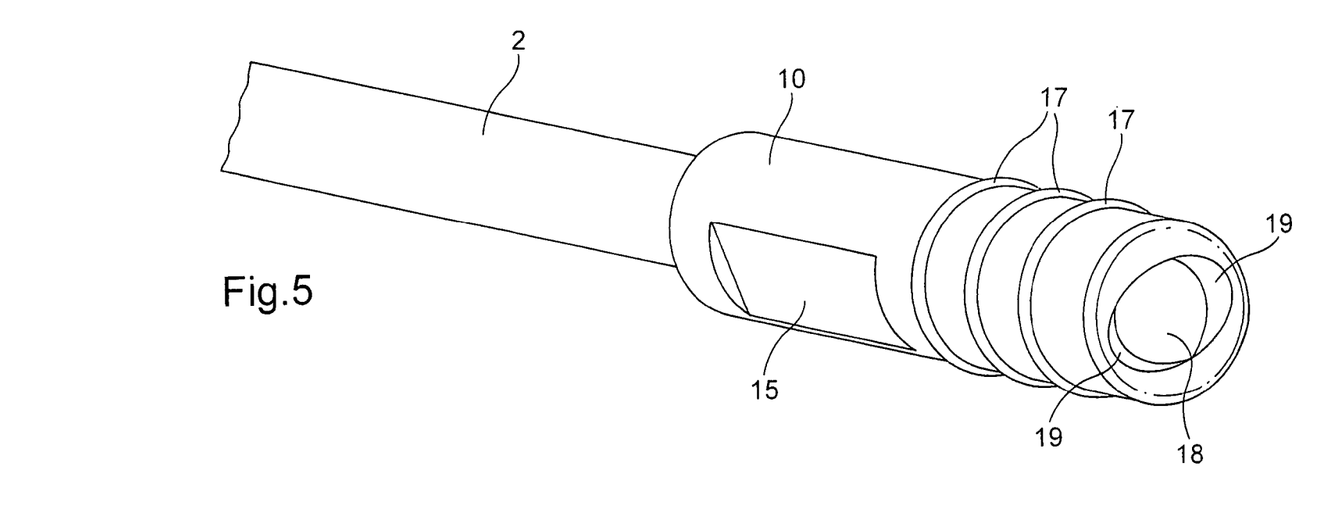
FIG. 5 shows the main hollow lance, provided with its sleeve, which is used in the take-off needle of FIGS. 1 to 4.

A first step consists of providing a main hollow lance 2 with a sleeve 10 to obtain the assembly represented in FIG. 5.

The hollow lance 2 is formed from a tube of stainless steel comprising an end adapted to form the proximal end of the hollow lance 2 (this is the end represented in FIG. 5). The sleeve 10 is molded onto this end in a mold of appropriate form in order for the sleeve 10 to have a cylindrical general form on which two flats 15, 16 of different length are formed (see FIG. 4), as well as three collars 17.

On molding the sleeve 10 onto the main hollow lance 2, a core of appropriate form enables there to be formed in addition an internal channel 18 in the sleeve 10 of cylindrical form extending in line with the hollow lance 2 and comprising, at the proximal end of the sleeve 10, two crescent-shaped surfaces 19 inclined towards the interior of the internal channel 18 and towards the distal end of the sleeve 10. This core, enabling the internal channel 18 and the surfaces 19 to be formed, is in the shape of a Y obtained by the joining together of three cylinders corresponding to the negative forms of the inner channel 18 and of the two pipes 12 (see FIG. 4).

Figure 6:
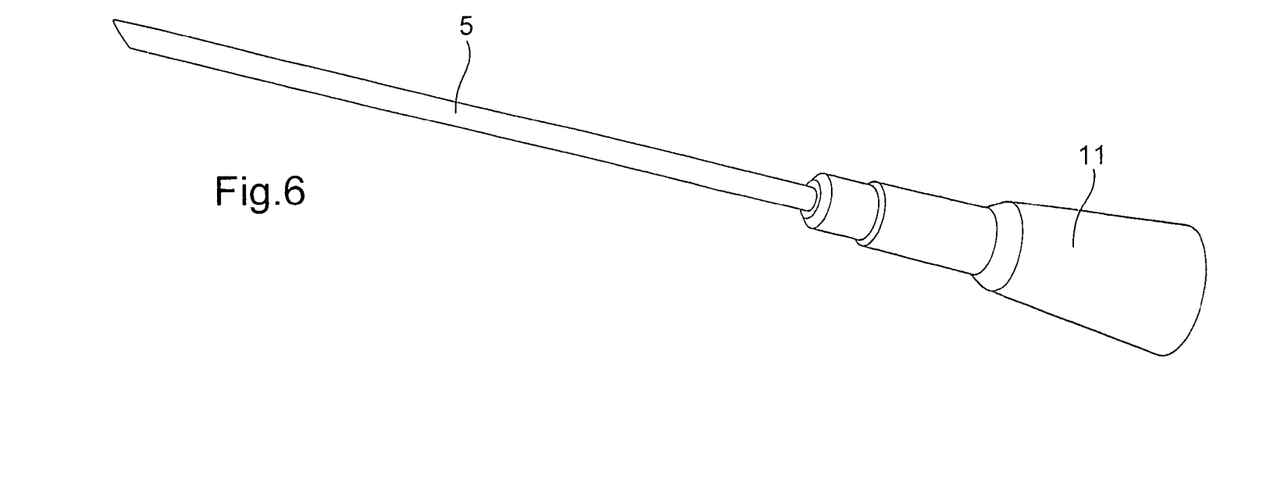
FIG. 6 is a perspective view of the venting hollow lance, provided with its support, which is used in the take-off needle of FIGS. 1 to 4.

With reference to FIG. 6, a second step consists of molding another sleeve, referred to here as support 11, onto a tube of stainless steel of diameter less than that forming the main hollow lance 2, this tube being adapted to form the venting hollow lance 5.

In the same way, the support 11 is molded onto the venting hollow lance 5 by virtue of a mold of appropriate form to give it the external form visible in FIG. 6, while an appropriate core enables the venting filter housing 13 (see FIG. 4) to be formed within the support 11.

Support 11 is such that the venting hollow lance 5 opens into the venting filter housing 13.

Figures 7, 8:
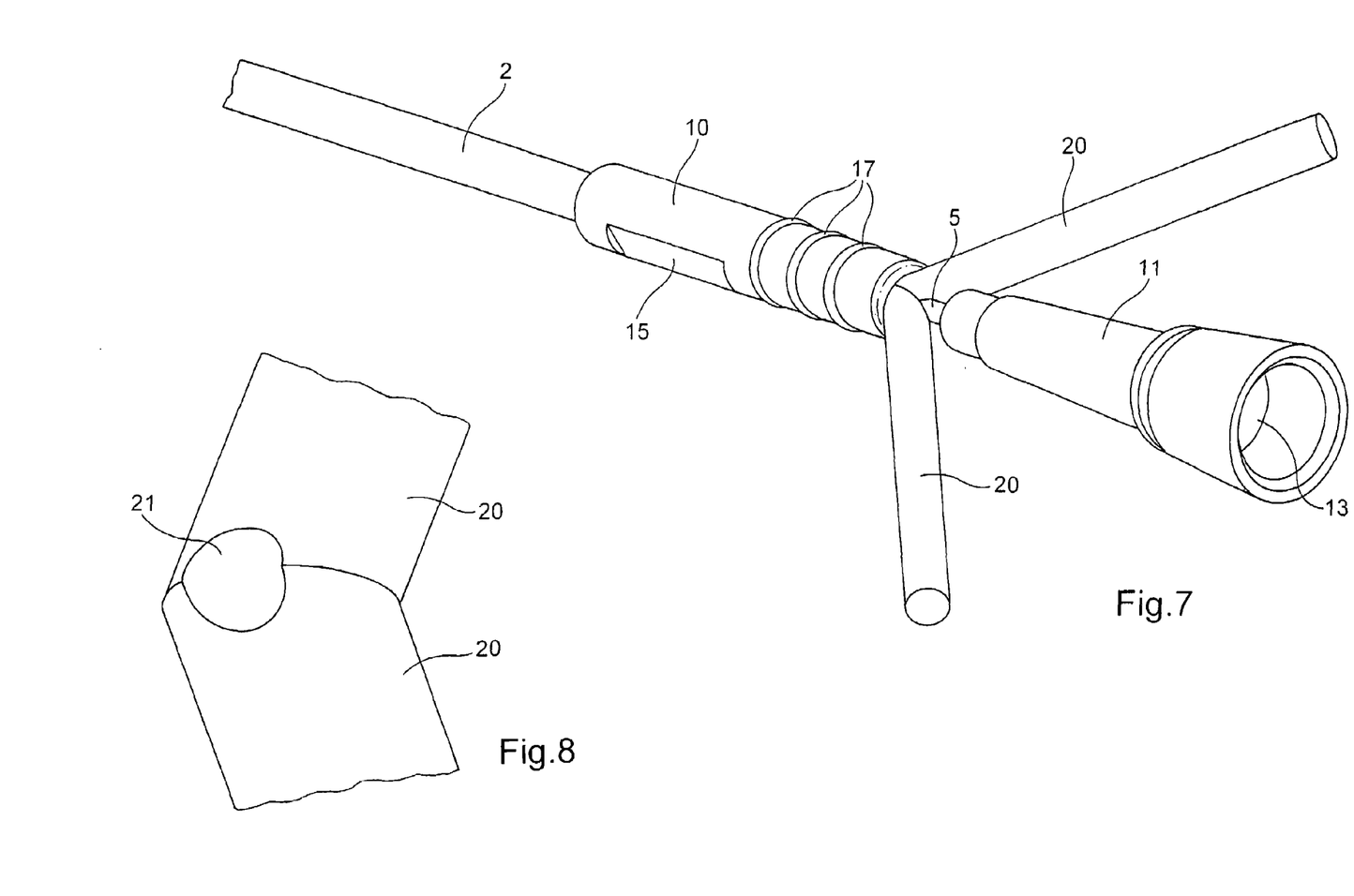
FIG. 7 is a perspective view of the hollow lances of FIGS. 5 and 6 arranged in cooperation with the pins in a V, this assembly enabling a holding body to be molded on to form the take-off needle of FIG. 3.
FIG. 8 is an enlarged view of the point of the V formed by the pins shown in FIG. 7.

The venting hollow lance 5 provided with its support 11 is then inserted into the main hollow lance 2, from the end with sleeve 10 in order to slide the venting hollow lance 5 inside the main hollow lance 2 (see FIG. 7).

With reference to FIGS. 7 to 10, the hollow lances 2, 5 are disposed in a mold in which an operation will be performed of molding on the holding body 8.

This mold (not shown) enables the precise positioning of the sleeve 10 with respect to the support 11 in the respective positions that these parts must occupy with respect to each other in the finished needle (see FIG. 4). The flats 15, 16 of the sleeve furthermore enables angular orientation of sleeve 10 about its longitudinal axis so as to locate the crescent-shaped surfaces 10 in a predetermined position.

FIG. 7 shows the result of the operation consisting of enclosing two cylindrical core pins 20 on the back of the sleeve. The two core pins 20 are beveled at their end so as to form a V when these two beveled ends are enclosed onto the venting hollow lance 5.

The beveled end of each core pin 20 furthermore comprises a duct enabling a passage 21 to be formed for the venting hollow lance 5 when the two core pins 20 are closed (see FIG. 8).

Figures 9, 10:
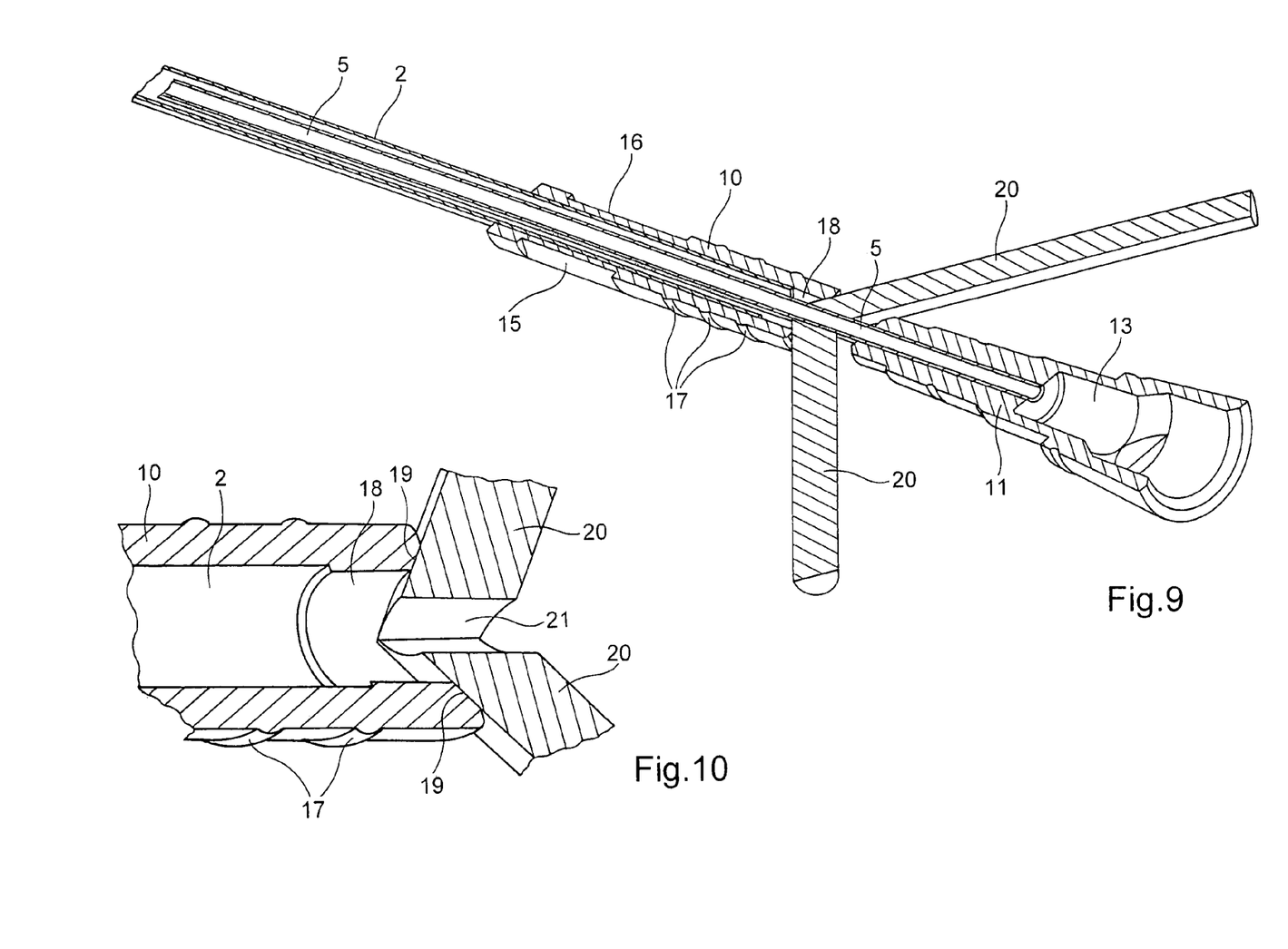
FIG. 9 is a longitudinal cross-section of the assembly of FIG. 7.
FIG. 10 is a detail view of the cooperation between the pins in a V and the sleeve of the main hollow lance.

FIG. 9 is a longitudinal cross-section of the assembly of FIG. 7 and shows in detail the cooperation of the core pins 20 once enclosed with the venting hollow lance 5 and the sleeve 10.

The V formed by the core pins 20 reproduces the form of the core which enabled the crescent-shaped surfaces 19 to be produced.

The core pins 20, when in the position of FIGS. 7 and 9, thus perfectly mates with the shape of the sleeve 10 at the crescent-shaped surfaces 19 (see FIG. 10, which is a detail view of FIG. 9, the venting hollow lance 5 not being shown in this Figure for greater clarity).

Preferably the sleeve 10 is made from polymer material and the core pins 20 are of metal such that the metal/polymer contact is fluid-tight.

Figure 11:
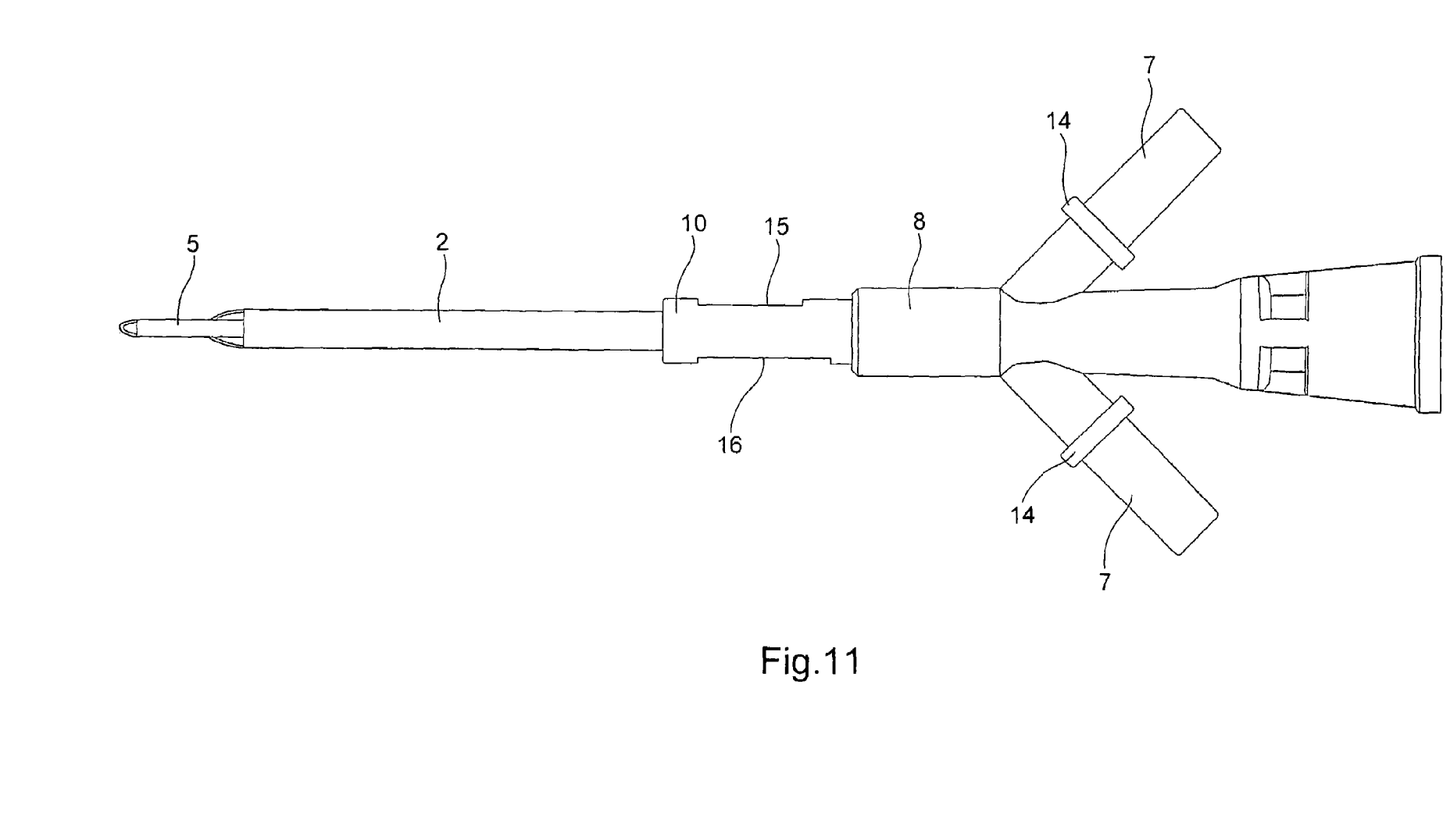
FIG. 11 shows the product obtained after the holding body is molded onto the assembly of FIG. 7, that is to say the take-off needle of FIG. 3.

The molding on of the holding body 8 is next performed in the mold which is adapted to form, around sleeve 10, support 11 and core pins 20, a holding body 8 of polymer in accordance with the external form in FIGS. 3 and 11.

The core pins 20 are then withdrawn along their longitudinal axis after having formed the internal cylindrical surfaces of the holding body 8 which define the pipes 12.

Figure 12:
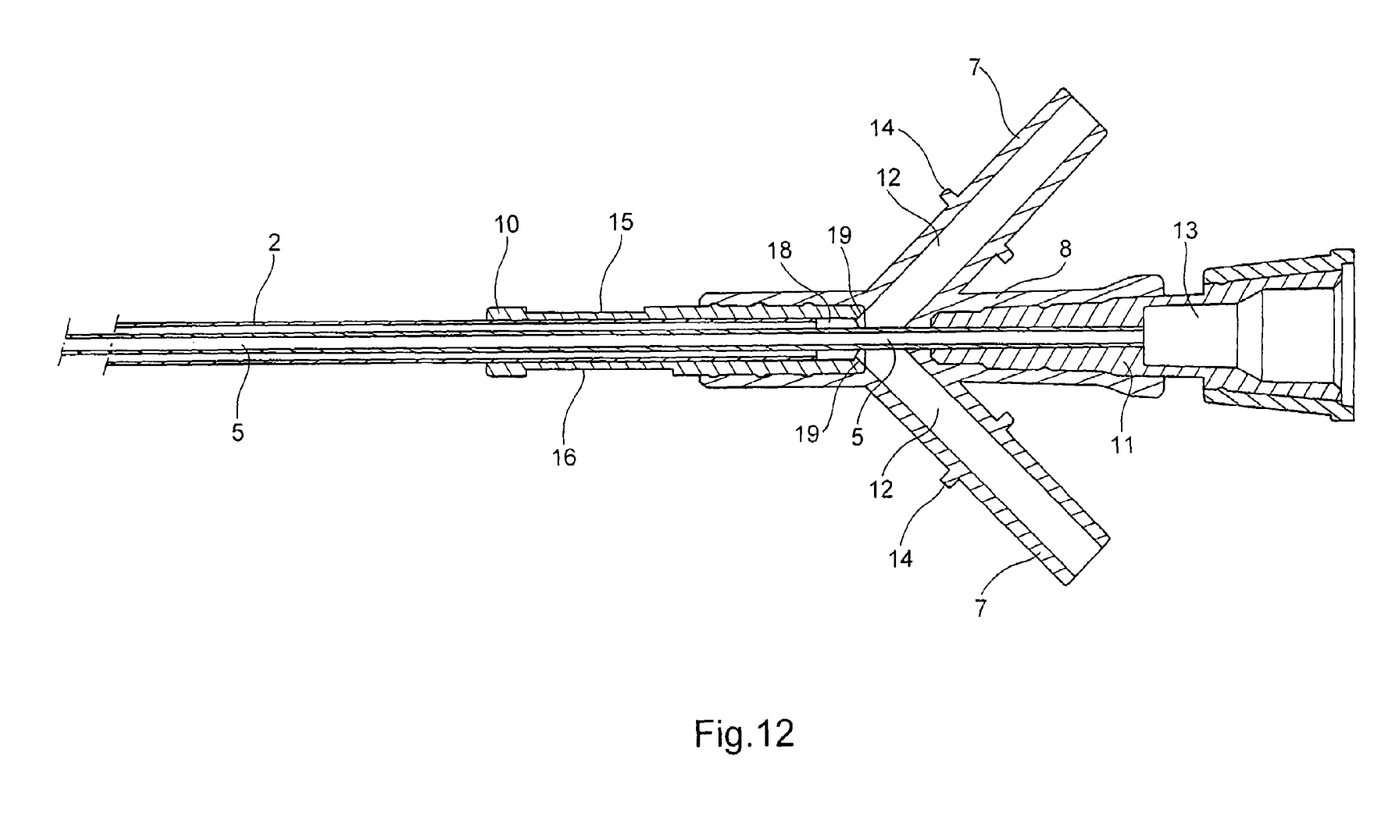
FIG. 12 is a longitudinal cross-section of the take-off needle as presented in FIG. 11.

FIG. 12, which is a longitudinal cross-section of the needle of FIG. 11, shows a plan view of the arrangement of the sleeve 10 and the support 11 as was set by the holding body 8 being molded on, the latter in addition defining the pipes 12.

This method consequently leads to the production of internal cylindrical surfaces (the pipes 12) extending partially into sleeve 10 (the crescent-shaped surfaces 19).

The view of FIG. 12 shows the crescent-shaped surfaces 10 in a position extending in line with the pipes 12.

Figure 13:
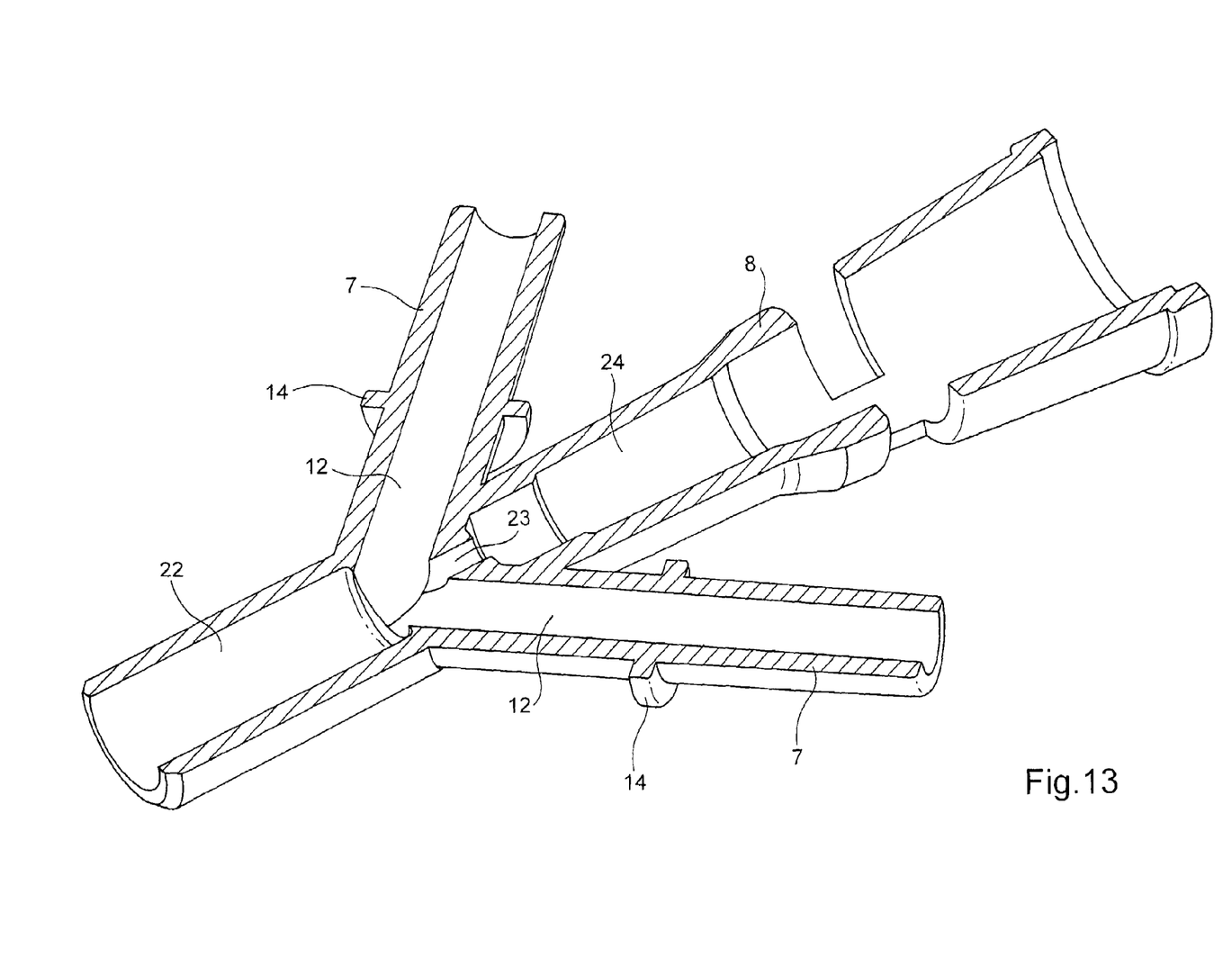
FIG. 13 is a perspective view in longitudinal cross-section of the holding body alone as molded onto the assembly of FIG. 7.
Figure 14:
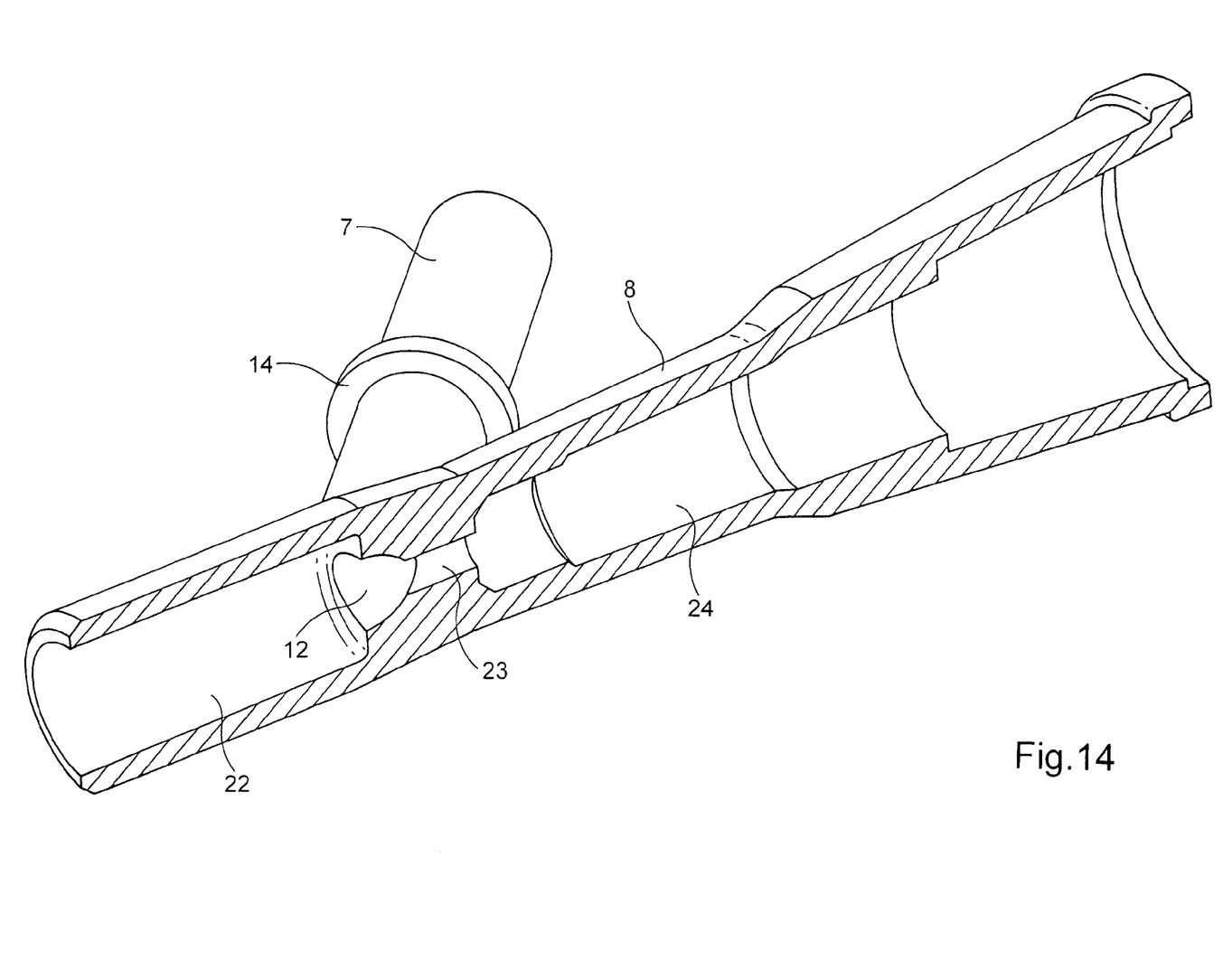
FIG. 14 is a perspective view in longitudinal cross-section of the holding body of FIG. 13, this longitudinal cross-section being made here along a plane perpendicular to the plane of the longitudinal cross-section of FIG. 13.

FIGS. 13 and 14 show the internal form of the holding body 8 obtained further to the operations described earlier.

The cross-section of FIG. 13 in a horizontal plane shows the communication between the pipes 12, a housing 22 receiving the sleeve 10, a connecting channel 23 adapted to receive the venting hollow lance 5, and a housing 24 for the support 11.

The housings 22, 24 and the connecting channel 23 are formed for fluid-tight reception of the respective member with which they are adapted to cooperate.

FIG. 14 shows the same members 22, 23, 24 when a cross-section is taken of the holding body 8 in a vertical plane.

Figure 15:
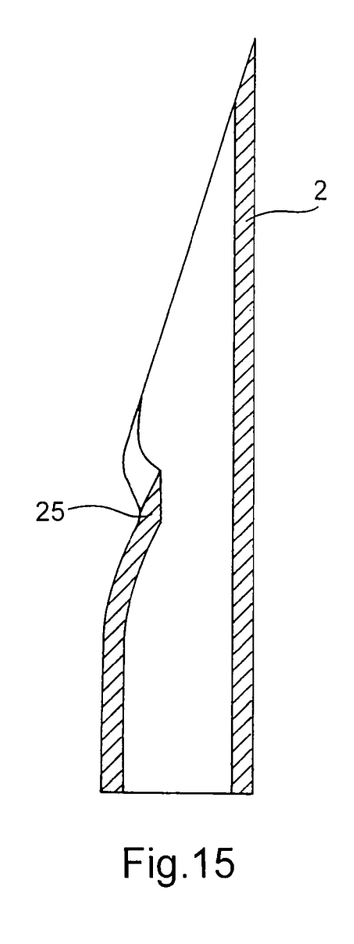
FIGS. 15 and 16 are views of the pricking tip of the main hollow lance, respectively in lateral cross-section, and from the front.
Figure 16:
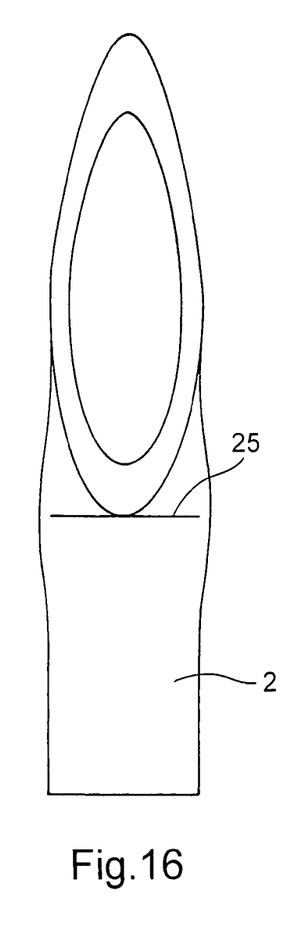

Furthermore, with reference to FIGS. 15 and 16, the sharpened distal tip of the main hollow lance 2, that is to say the end which is adapted to perform a pricking operation, may be produced with a crushed heel 25 making it possible to limit the diameter of the opening of the beveled point of the main hollow lance 2. This provision makes it possible to avoid "coring", that is to say that it makes it possible to avoid cutting out a cylinder from the bung 3 of the bottle 4, at the time of piercing, that rubber cylinder potentially blocking the main hollow lance 2.

The crushed heel 25 may advantageously be produced at the time of the operation of molding on the holding body 8 by situating a punch in the mold providing that molding-on operation. The punch may be actuated to strike the main hollow lance 2 when the latter is placed in the mold.

Variant embodiments of the take-off needle described and of its method of manufacture may be envisaged without departing from the scope of the invention. In particular, methods of plastic deformation may be implemented to form the crescent-shaped surfaces 19.

What is claimed is:

1. A take-off needle comprising a main hollow lance having a distal end adapted to perform a pricking operation, said hollow lance being connected to two pipes, each provided with a spigot for it to be connected to a tube, said needle having a body for holding the main hollow lance, said holding body having an interior geometry defining two internal cylindrical surfaces forming said pipes and in that the main hollow lance comprises, at its proximal end, a sleeve having an internal channel of which the distal end is connected to the proximal end of the main hollow lance and of which the proximal end opens into the holding body, said sleeve comprising at its proximal end two crescent-shaped surfaces adjacent the internal channel and inclined towards the interior of the internal channel and towards the distal end of the sleeve, each of said crescent-shaped surfaces being disposed so as to extend in line with one of the internal cylindrical surfaces through the interior geometry of the holding body.

2. The take-off needle according to claim 1, wherein the sleeve extends beyond the proximal end of the main hollow lance, the crescent-shaped surfaces being disposed away from the proximal end of the main hollow lance.

3. The take-off needle according to claim 1 further comprising a venting hollow lance inserted coaxially in the main hollow lance, the venting hollow lance passing through the internal channel of the sleeve.

4. The take-off needle according to claim 1 further comprising a venting hollow lance inserted coaxially in the main hollow lance, the venting hollow lance passing through the internal channel of the sleeve and the venting hollow lance comprises a support at its proximal end, the support being fixed to the holding body.

5. The take-off needle according to claim 1 further comprising a venting hollow lance inserted coaxially in the main hollow lance, the venting hollow lance passing through the internal channel of the sleeve and the venting hollow lance comprises a support at its proximal end, the support being fixed to the holding body and the support is molded onto the proximal end of the venting hollow lance.

6. The take-off needle according to claim 1 further comprising a venting hollow lance inserted coaxially in the main hollow lance, the venting hollow lance passing through the internal channel of the sleeve and the venting hollow lance comprises a support at its proximal end, the support being fixed to the holding body and the holding body is molded onto the sleeve and onto the support.

7. The take-off needle according to claim 1 further comprising a venting hollow lance inserted coaxially in the main hollow lance, the venting hollow lance passing through the internal channel of the sleeve and the venting hollow lance comprises a support at its proximal end, the support being fixed to the holding body and the holding body comprises a housing in which the sleeve is held; two pipes communicating with said housing; a housing for the support; said housings being aligned.

8. The take-off needle according to claim 1 further comprising a venting hollow lance inserted coaxially in the main hollow lance, the venting hollow lance passing through the internal channel of the sleeve and the venting hollow lance comprises a support at its proximal end, the support being fixed to the holding body and the holding body comprises a housing in which the sleeve is held; two pipes communicating with said housing; a housing for the support; said housings being aligned and the holding body further comprises a connecting channel receiving the venting hollow lance and communicating with the two pipes.

9. The take-off needle according to one of claim 1 wherein the sleeve is elastically deformable.

10. The take-off needle according to claim 1 wherein the main hollow lance comprises a crushed heel at its distal end.

11. A method of manufacturing a take-off needle comprising a main hollow lance having a distal end adapted to perform a pricking operation, said hollow lance being connected to two pipes, each provided with a spigot for it to be connected to a tube, said needle having a body for holding the main hollow lance, said holding body defining two internal cylindrical surfaces forming said pipes and in that the main hollow lance comprises, at its proximal end, a sleeve having an internal channel of which the distal end is connected to the proximal end of the main hollow lance and of which the proximal end opens into the holding body, said sleeve comprising at its proximal end two crescent-shaped surfaces adjacent the internal channel and inclined towards the interior of the internal channel and towards the distal end of the sleeve, each of said crescent-shaped surfaces being disposed so as to extend in line with one of the internal cylindrical surfaces of the holding body, the method comprising the following steps:
   molding the sleeve onto the main hollow lance using a Y-shaped core adapted to form the crescent-shaped surfaces on the sleeve;
   molding the holding body onto the sleeve using two cylindrical core pins forming a V of the same form as said core.

12. A take-off needle comprising a main hollow lance having a distal end adapted to perform a pricking operation, said hollow lance being connected to two pipes, each provided with a spigot for it to be connected to a tube, said needle having a body for holding the main hollow lance, said holding body defining two internal cylindrical surfaces forming said pipes and in that the main hollow lance comprises, at its proximal end, a sleeve having an internal channel of which the distal end is connected to the proximal end of the main hollow lance and of which the proximal end opens into the holding body, said sleeve comprising at its proximal end two crescent-shaped surfaces adjacent the internal channel and inclined towards the interior of the internal channel and towards the distal end of the sleeve, each of said crescent-shaped surfaces being disposed so as to extend in line with one of the internal cylindrical surfaces of the holding body and wherein the main hollow lance comprises a crushed heel at its distal end.

* * * * *

UNITED STATES PATENT AND TRADEMARK OFFICE
CERTIFICATE OF CORRECTION

PATENT NO. : 7,645,270 B2  Page 1 of 1
APPLICATION NO. : 11/247523
DATED : January 12, 2010
INVENTOR(S) : Geyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 903 days.

Signed and Sealed this

Sixteenth Day of November, 2010

David J. Kappos
*Director of the United States Patent and Trademark Office*